United States Patent [19]

Farges et al.

[11] 4,271,290

[45] Jun. 2, 1981

[54] 3,4-XYLIDINE-N-RIBITYL

[75] Inventors: Guy Farges, Montlucon; Anne-Marie Michard, Commentry, both of France

[73] Assignee: A.E.C. Societe de Chimie Organique et Biologique, Commentry, France

[21] Appl. No.: 48,099

[22] Filed: Jun. 13, 1979

[30] Foreign Application Priority Data

Jun. 15, 1978 [FR] France ................................ 78 17905

[51] Int. Cl.³ .............................................. C07H 5/06
[52] U.S. Cl. ........................................ 536/22; 536/18
[58] Field of Search .............................. 536/18, 22, 23

[56] References Cited

U.S. PATENT DOCUMENTS

| 2,384,105 | 9/1945 | Lee et al. | 536/18 |
| 2,422,997 | 6/1947 | Wuest | 536/18 |
| 2,429,244 | 10/1947 | Spiegelberg | 536/18 |
| 2,477,560 | 8/1949 | Aaron et al. | 536/18 |
| 3,332,935 | 7/1967 | Yamazaki et al. | 536/23 |
| 4,071,680 | 1/1978 | Cook | 536/22 |

FOREIGN PATENT DOCUMENTS 941179  6/1948  France ........................ 536/18

*Primary Examiner*—Johnnie R. Brown
*Attorney, Agent, or Firm*—Stevens, Davis, Miller & Mosher

[57] ABSTRACT

N-[2,3-(O-Isopropylidene)-(D)-ribityl]-3,4-xylidine is a new compound, which can be used as an intermediate for the preparation of N-(D)-ribityl-3,4-xylidine.

2 Claims, No Drawings

3,4-XYLIDINE-N-RIBITYL

This invention relates to a new 3,4-xylidine derivative, its preparation and its use.

The new 3,4-xylidine derivative of the present invention, which is N-[2,3-(O-isopropylidene)-(D)-ribityl]-3,4-xylidine of the formula:

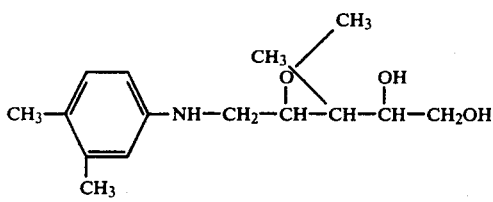

can be used as a synthesis intermediate, in particular for the preparation of N-(D)-ribityl-3,4-xylidine of formula (VI) hereafter.

N-(D)-Ribityl-3,4-xylidine is commonly prepared from D(+)-glucose by a complex process which initially leads to a mixture of D(+)-ribono-γ-lactone (II, intermediate) and D(+)-arabono-γ-lactone (III, by-product) of the respective formulae:

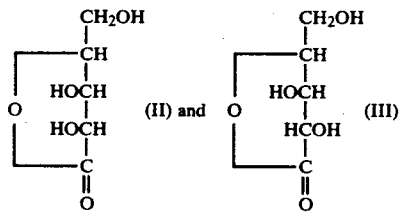

The D(+)-ribono-γ-lactone is then reduced (by sodium amalgam or by electrolytic reduction on a mercury cathode) to give D(−)-ribose (IV) which reacts with 3,4-xylidine to give 3,4-xylidine N-(D)-ribopyranoside (V), and this product is reduced to give N-(D)-ribityl-3,4-xylidine (VI) using hydrogen in the presence of palladium on charcoal. The reaction scheme is as follows:

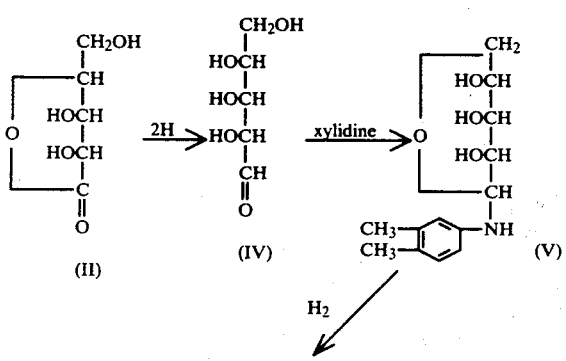

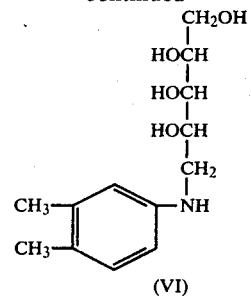

In this process, it is possible either to separate off the D(+)-arabono-γ-lactone before the reduction of the ribonolactone to give ribose, or not to carry out the purification until after the reaction with 3,4-xylidine, at the expense of an additional consumption of this reactant due to the by-product.

The 3,4-xylidine derivative of the present invention can be prepared by reacting 2,3-(O-isopropylidene)-D(+)-ribono-γ-lactone of formula (VII)

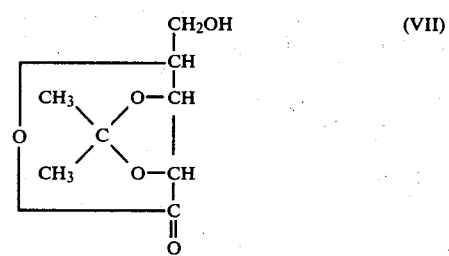

with 3,4-xylidine in the presence of an alkali metal borohydride (preferably sodium borohydride) and an acid.

According to a first variant, the reaction is carried out in a non-hydroxylic organic solvent (such as 1,2-dimethoxyethane, dioxan or tetrahydrofuran) which is essentially anhydrous, i.e. contains less than 1% of water by weight. The acid used is preferably an anhydrous carboxylic acid, the pK of which is less than or equal to 5.2, and which is soluble in the reaction medium (e.g. acetic, propionic or pivalic acid). The reaction is generally carried out at between 10° and 50° C., and preferably from 20° to 30° C., using 1 to 2 mols (preferably about 1.5 mols) of 3,4-xylidine, 2 to 2.2 mols of borohydride and 2 to 2.2 mols of acid for each mol of lactone of formula (VII).

No substantial advantage is gained by using an excess of borohydride relative to the lactone. On the other hand, the acid and the borohydride must be in approximately equimolecular proportions.

According to a second variant, the reaction is carried out in an organic solvent containing from 1 to 66% of water at a temperature of from 0° to 25° C. (preferably 0° to 5° C.) and at a pH between 4 and 7 (preferably from 6 to 7). 1 to 2 Mols of xylidine and 1.5 to 2 mols of borohydride are used for each mol of lactone. The acid can be an acid defined in the first variant or a non-oxidising inorganic acid in aqueous solution, e.g. sulphuric or hydrochloric acid.

Under these conditions, N-[2,3-(O-isopropylidene)-ribofuranoside]-3,4-xylidine of formula (VIII) is formed as an intermediate.

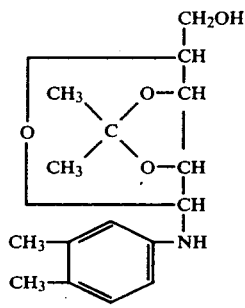

(VIII)

This product leads to N-[2,3-(O-isopropylidene)-ribityl]-3,4-xylidine by reduction, in an aqueous-alcoholic medium, preferably an aqueous-methanolic medium, by means of hydrogen (in the presence of palladium on charcoal or of Raney nickel), by means of sodium acetoxyborohydride [prepared in accordance with T. Reetz, J. Amer. Chem. Soc., 82, 5039 (1960), from sodium borohydride and acetic acid] or by means of an approximately equimolecular mixture of borohydride and acetic acid.

The product of formula (VIII) is also formed, in addition to N-[2,3-(O-isopropylidene)-(D)-ribityl]-3,4-xylidine, if the non-hydroxylic solvent contains more than 1% of water, and occurs in that case as a recoverable by-product.

2,3-(O-Isopropylidene)-D(+)-ribono-γ-lactone can be prepared as described in Japanese Patent Application published under No. 27821/70 (Chem. Abstracts, 1971, 74, 23109/j) by reacting acetone with the abovementioned mixture of D(+)-ribono-γ-lactone and D(+)-arabono-γ-lactone.

The compound of this invention can be converted to N-(D)-ribityl-3,4-xylidine by acid hydrolysis, for example by heating in the presence of aqueous hydrochloric acid. The duration of the treatment depends on the temperature and the acidity, one hour being sufficient when the reaction is carried out under reflux at pH 1.

The N-(D)-ribityl-3,4-xylidine can be isolated by crystallisation after neutralisation of the reaction mixture.

The compound of this invention proves advantageous because it can be prepared in a simple manner from D(+)-ribono-γ-lactone by using readily accessible reducing agents, without requiring the use of mercury or its derivatives, and because it can be directly converted to N-(D)-ribityl-3,4-xylidine.

The preparation of N-(D)-ribityl-3,4-xylidine from a mixture of D(+)-ribono-γ-lactone and D(+)-arabono-γ-lactone, via the compound of the invention, requires only three steps, one of which is a reduction step, whereas the previously known process requires four steps comprising two separate reduction steps.

The following Examples illustrate the invention.

EXAMPLE 1

Direct preparation.

2,3-(O-Isopropylidene)-ribono-γ-lactone (5 g, $26.6 \times 10^{-3}$ mols), 3,4-xylidine (4.8 g, $39.9 \times 10^{-3}$ mols) and anhydrous dioxan (40 cc) are introduced into a round-bottomed flask (250 cc) equipped with a magnetic stirrer, and the mixture is stirred at the temperature of the laboratory (20° C.). Sodium borohydride (0.7 g) and glacial acetic acid (1.1 cc) are added separately at the same time, then, after stirring for 2 hours, the same reactants (0.7 g and 1.1 cc) are added, and then, after 2 hours, the same reactants (0.7 g and 1.0 cc) are added (a total of $55.3 \times 10^{-3}$ mols of $NaBH_4$ and $56.0 \times 10^{-3}$ mols of acetic acid).

The mixture is stirred for a further 22 hours at about 20° C. and filtered in order to separate off the precipitate which is washed with absolute ethanol (5 cc). The filtrate and the washings are evaporated to dryness and the residue is taken up in water (50 cc) and extracted with diethyl ether (2 × 50 cc).

After evaporation of the ether extracts, a syrup (8.8 g) is obtained which contains N-[2,3-(O-isopropylidene)-(D)-ribityl]-3,4-xylidine (67%) and 3,4-xylidine (20%) (high-pressure liquid chromatography). This mixture can be used directly for the preparation of of N-(D)-ribityl-3,4-xylidine.

A syrup prepared in the same manner is fractionated by high-performance liquid-phase chromatography on silica, elution being carried out with a diisopropyl ether/hexane/methanol mixture (50/45/5 by volume, water content 0.26%). Pure N-[2,3(O-isopropylidene)-(D)-ribityl]-3,4-xylidine is thus obtained.

$[\alpha]_{D25} = +11.6°$ (c=5, chloroform)

| UV spectrum (isopropanol): | |
|---|---|
| $E_1^{1\%}$ cm | 244 nm: 346 |
| | 295 nm: 52 |

EXAMPLE 2

Indirect preparation.

(A) 2,3-(O-Isopropylidene)-ribono-γ-lactone (20 g, 0.106 mol), water (200 cc), 3,4-xylidine (12.82 g, 0.106 mol) and ethanol (140 cc) are introduced into a round-bottomed flask (500 cc) equipped with a magnetic stirrer, a thermometer and a pH meter. A yellow solution of pH 6.8 is obtained. It is cooled to between 0° and 5° C. and sodium borohydride (6.4 g, 0.168 mol) is added in the course of 1 hour, whilst keeping the pH at between 6 and 7 by adding acetic acid. The temperature is then allowed to rise to 20°-25° C. and stirring is maintained for 3 hours. A white precipitate appears. The mixture is cooled to 10°-15° C. for 1 hour and the precipitate is isolated by filtration and washed with a water/ethanol solution (200/140 by volume).

A first fraction (13.48 g) of N-[2,3-(O-isopropylidene)-(D)-ribofuranoside]-3,4-xylidine, which melts at 128° C., is thus obtained.

$[\alpha]_D^{25} = +23°$ (c=5, methanol)

By continuing the cooling, a second fraction (3.69 g) is obtained from the mother liquor.

(B) N-[2,3-(O-Isopropylidene)-(D)-ribofuranoside]-3,4-xylidine (20 g, 0.068 mol), methanol (280 cc) and water (120 cc) are introduced into a glass hydrogenation apparatus (1 liter) placed on a shaker. The mixture is heated at 55°-60° C. until dissolution takes place, and catalyst (4 g) containing palladium on charcoal (5%) is added. Hydrogenation is carried out for 7 hours at 55°-60° C. at a pressure in the region of atmospheric pressure. After hot filtration and evaporation to dryness, a syrup (20.49 g) is obtained which consists of N-[2,3-(O-isopropylidene)-(D)-ribityl]-3,4-xylidine (95%) (potentiometric determination).

EXAMPLE 3

Use.

The product obtained in accordance with Example 1 is taken up in water (50 cc) and the solution is acidified to pH 1 by adding concentrated hydrochloric acid (4 cc).

The mixture is heated under reflux for 1 hour and then neutralised to pH 7 to 8 by adding aqueous sodium hydroxide solution (30% strength by weight). N-(D)-Ribityl-3,4-xylidine precipitates. The mixture is cooled at 4° C. overnight and the product is filtered off and dried. N-(D)-Ribityl-3,4-xylidine (4.86 g), is obtained, which melts at 142° C., has a purity of 99.7% and is suitable for the synthesis of riboflavin.

A product (2.44 g) containing xylidine (80%) can be recovered from the mother liquors (by extraction with diethyl ether and evaporation).

We claim:

1. N-[2,3-(O-Isopropylidene)-(D)-ribityl]-3,4-xylidine of the formula

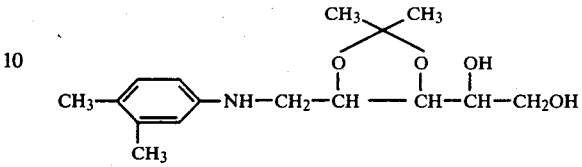

2. N-[2,3-(O-Isopropylidene)-ribofuranoside]-3,4-xylidine.

* * * * *